US008518377B2

(12) United States Patent
Hoelz et al.

(10) Patent No.: US 8,518,377 B2
(45) Date of Patent: Aug. 27, 2013

(54) AEROSOL SUSPENSION FORMULATIONS WITH TG 227 EA OR TG 134 A AS PROPELLANT

(75) Inventors: Hubert Hoelz, Oberheimbach (DE); Mariola Mann, Bingen (DE); Christel Schmelzer, Ingelheim am Rhein (DE); Friedrich Schmidt, Ingelheim am Rhein (DE); Hans-Hermann Weil, Gau-Bickelheim (DE)

(73) Assignee: Boehringer Ingelheim Pharma GbmH Co. KG, Ingelheim am Rhein (DE)

( * ) Notice: Subject to any disclaimer, the term of this patent is extended or adjusted under 35 U.S.C. 154(b) by 502 days.

(21) Appl. No.: 12/296,473

(22) PCT Filed: Apr. 4, 2007

(86) PCT No.: PCT/EP2007/053333
§ 371 (c)(1),
(2), (4) Date: Dec. 9, 2008

(87) PCT Pub. No.: WO2007/118802
PCT Pub. Date: Oct. 25, 2007

(65) Prior Publication Data
US 2009/0092559 A1    Apr. 9, 2009

(30) Foreign Application Priority Data
Apr. 11, 2006 (DE) .................. 10 2006 017 320

(51) Int. Cl.
*A61K 9/12* (2006.01)
(52) U.S. Cl.
USPC .................................................. 424/45
(58) Field of Classification Search
USPC .................................................. 424/45
See application file for complete search history.

(56) References Cited

U.S. PATENT DOCUMENTS

| | | | |
|---|---|---|---|
| 5,225,183 A | 7/1993 | Purewal et al. | |
| 5,676,930 A | 10/1997 | Jager et al. | |
| 5,682,875 A | 11/1997 | Blower et al. | |
| 5,836,299 A | 11/1998 | Kwon | |
| 5,919,435 A | 7/1999 | Taylor et al. | |
| 5,955,058 A | 9/1999 | Jager et al. | |
| 6,036,942 A | 3/2000 | Alband | |
| 6,045,778 A | 4/2000 | Jager et al. | |
| 6,092,696 A | 7/2000 | Thomas | |
| 6,234,362 B1 | 5/2001 | Thomas | |
| 6,261,539 B1 | 7/2001 | Adjei et al. | |
| 6,305,371 B1 | 10/2001 | Frid et al. | |
| 6,306,368 B1 | 10/2001 | Taylor et al. | |
| 6,423,298 B2 * | 7/2002 | McNamara et al. ............ 424/45 |
| 6,475,467 B1 | 11/2002 | Keller et al. | |
| 6,511,652 B1 | 1/2003 | Ashurst et al. | |
| 6,739,333 B1 | 5/2004 | Hoelz et al. | |
| 6,983,743 B2 | 1/2006 | Hoelz et al. | |
| 7,776,315 B2 * | 8/2010 | Pairet et al. ...................... 424/46 |
| 7,914,770 B2 | 3/2011 | DeStefano et al. | |
| 2001/0031244 A1 | 10/2001 | Lewis et al. | |
| 2002/0076382 A1 | 6/2002 | Kaplan et al. | |
| 2002/0122826 A1 | 9/2002 | Lizio et al. | |
| 2003/0018019 A1 * | 1/2003 | Meade et al. .................. 514/171 |
| 2003/0066525 A1 | 4/2003 | Lewis et al. | |
| 2003/0089368 A1 | 5/2003 | Zhao | |
| 2003/0089369 A1 | 5/2003 | Lewis et al. | |
| 2003/0190287 A1 | 10/2003 | Lewis et al. | |
| 2003/0206870 A1 | 11/2003 | Lewis et al. | |
| 2004/0184994 A1 * | 9/2004 | DeStefano et al. ............. 424/45 |
| 2005/0118107 A1 * | 6/2005 | Burns et al. ..................... 424/45 |
| 2005/0129621 A1 | 6/2005 | Davies et al. | |
| 2005/0152846 A1 * | 7/2005 | Davies et al. ................... 424/46 |
| 2006/0002863 A1 * | 1/2006 | Schmelzer et al. ............. 424/46 |
| 2007/0183982 A1 * | 8/2007 | Berkel et al. ..................... 424/40 |
| 2009/0092559 A1 | 4/2009 | Hoelz et al. | |
| 2011/0014134 A1 * | 1/2011 | Weil et al. ....................... 424/45 |

FOREIGN PATENT DOCUMENTS

| | | |
|---|---|---|
| DE | 032322 A1 | 2/2006 |
| EP | 0990437 A1 | 4/2000 |
| EP | 1219293 A2 | 7/2002 |
| EP | 1241113 A1 | 9/2002 |
| EP | 1527772 A1 | 5/2005 |
| WO | 9315741 A1 | 8/1993 |
| WO | 9413262 A1 | 6/1994 |
| WO | 9502651 A1 | 1/1995 |
| WO | 9701611 A1 | 1/1997 |
| WO | 9856349 A1 | 12/1998 |
| WO | 9965464 A1 | 12/1999 |

(Continued)

OTHER PUBLICATIONS

Google (search results for "salbutamol albuerol betamimetic") [Downloaded May 22, 2011] [Retrieved from internet <URL:http://www.google.com/search?q=COPD&sourceid=ie7&rls=com.microsoft:en-us:IE-SearchBox&ie=&oe=#sclient=psy&h1=en&rls=com.microsoft:en-us%3AIE-SearchBox&biw=1053&bih=677&source=hp&q=salbutamol+albuterol+betamimetic&aq=f&aqi=&aql=&oq=&pbx=1&bav=on.2,or.r_gc.r_pw.&fp=e5b130cc10bf5fa1 >] (2 pages).*
Form PCT-IB-373—International Preliminary Report on Patentability.
Form PCT-ISA-237—Written Opinion of the International Searching Authority.
Williams, R.O., et al., Influence of Metering Chamber Volume and Water Level on the Emitted Dose of a Suspension-based pMDI Containing Profellant 134a; Pharmaceutical Research, 1997, vol. 14, No. 4, pp. 438-443.
International Search Report for PCT/EP2007/053333.

*Primary Examiner* — Jason M Sims
*Assistant Examiner* — Miriam A Levin
(74) *Attorney, Agent, or Firm* — Michael P. Morris; Anthony P. Bottino

(57) ABSTRACT

The invention relates to pressurized gas formulations for dosage aerosols, in which a medicament is formulated suspended in TG 227 ea (1,1,1,2,3,3,3-heptafluoropropane) and/or TG 134 a (1,1,1,2-tetrafluoroethane) as a propellant, and to their use for producing a medicament. The aerosol is preferably an inhalation aerosol.

23 Claims, No Drawings

(56) References Cited

FOREIGN PATENT DOCUMENTS

| | | |
|---|---|---|
| WO | 0030607 A1 | 6/2000 |
| WO | 0030608 A1 | 6/2000 |
| WO | 0033892 A1 | 6/2000 |
| WO | 025785 A1 | 1/2002 |
| WO | 0217882 A1 | 3/2002 |
| WO | 03002169 A2 | 1/2003 |
| WO | 2004084858 A2 | 10/2004 |
| WO | 2006002840 A2 | 1/2006 |
| WO | 2006064283 A1 | 6/2006 |
| WO | 2007118802 A1 | 10/2007 |

* cited by examiner

AEROSOL SUSPENSION FORMULATIONS WITH TG 227 EA OR TG 134 A AS PROPELLANT

APPLICATION DATA

This application is a 371 National Stage filing of PCT/EP2007/053333 filed Apr. 4, 2007, in Germany, which claims priority to a foreign application number DE 102006017320, filed Apr. 11, 2006, in Germany, the entire disclosure of which is incorporated herein by reference.

The invention relates to pressurised gas preparations for metered-dose aerosols, wherein a medicament is formulated as a suspension in TG 227 ea (1,1,1,2,3,3,3-heptafluoropropane) and/or TG 134 a (1,1,1,2-tetrafluoroethane) as propellant, and the use thereof for preparing a medicament. Preferably it relates to an inhalable aerosol.

PRIOR ART

It has been known since the early 1990s that the propellant gases TG 227 ea or TG 134 a may be used as alternative propellant gases to chlorofluorocarbons for inhalable aerosols.

It has now been found that, surprisingly, propellant gas formulations with suspended particles of active substance and TG 227 ea and/or TG 134 a as propellant exhibit reduced separation of the active substances in the suspension if special surface-active substances (surfactants) are used.

DETAILED DESCRIPTION OF THE INVENTION

For the propellant formulations according to the invention TG 227 ea and/or TG 134 a are used as propellant gases, optionally in admixture with one or more other propellant gases, preferably selected from among propane, butane, pentane, dimethylether, $CHClF_2$, $CH_2F_2$, $CF_3CH_3$, isobutane, isopentane and neopentane.

Preferred suspensions according to the invention are those which contain as propellant gas only TG 227 ea or only TG 134 a.

If a mixture of the propellant gases TG 227 ea and TG 134a is used in the suspension formulations according to the invention, the proportions by weight in which these two propellant gas components may be used may be freely variable, although TG 227 ea must be present.

In mixtures with one or more other propellant gases, selected from among propane, butane, pentane, dimethylether, $CHClF_2$, $CH_2F_2$, $CF_3CH_3$, isobutane, isopentane and neopentane, the proportion of this other propellant gas component is preferably less than 60%, preferably below 40% and most preferably less than 30%.

The active substances used are preferably active substances which incorporate or bind one or more water molecules in their particle structure. The water is not only physically mixed with the particles of active substance. Preferably the particles of active substance are crystals and the water is water of crystallisation or complex-bound water or water which is otherwise chemically bound, e.g. hydrates. This form of water incorporation is hereinafter also referred to as chemically bound water. In these cases the water generally also affects the crystalline structure of the active substance molecule.

Preferably, compounds that are effective by inhalation are used, with the result that the suspension formulations according to the invention are preferably intended for inhalation.

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1,1dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol
2-hydroxy-5-(1-hydroxy-2-{2-[4-(2-hydroxy-2-phenyl-ethylamino)-phenyl]-ethylamino}-ethyl)-benzaldehyde
N-[2-hydroxy-5-(1-hydroxy-2-{2-[4-(2-hydroxy-2-phenyl-ethylamino)-phenyl]-ethylamino}-ethyl)-phenyl]-formamide
8-hydroxy-5-(1-hydroxy-2-{2-[4-(6-methoxy-biphenyl-3-ylamino)-phenyl]-ethylamino}-ethyl)-1H-quinolin-2-one
8-hydroxy-5-[1-hydroxy-2-(6-phenethylamino-hexylamino)-ethyl]-1H-quinolin-2-one
5-[2-(2-{4-[4-(2-amino-2-methyl-propoxy)-phenylamino]-phenyl}-ethylamino)-1-hydroxy-ethyl]-8-hydroxy-1H-quinolin-2-one
[3-(4-{6-[2-hydroxy-2-(4-hydroxy-3-hydroxymethyl-phenyl)-ethylamino]-hexyloxy}-butyl)-5-methyl-phenyl]-urea
4-(2-{6-[2-(2,6-dichloro-benzyloxy)-ethoxy]-hexylamino}-1-hydroxy-ethyl)-2-hydroxymethyl-phenol
3-(4-{6-[2-hydroxy-2-(4-hydroxy-3-hydroxymethyl-phenyl)-ethylamino]-hexyloxy}-butyl)-benzylsulphonamide
3-(3-{7-[2-hydroxy-2-(4-hydroxy-3-hydroxymethyl-phenyl)-ethylamino]-heptyloxy}-propyl)-benzylsulphonamide
4-(2-{6-[4-(3-cyclopentanesulphonyl-phenyl)-butoxy]-hexylamino}-1-hydroxy-ethyl)-2-hydroxymethyl-phenol
N-Adamantan-2-yl-2-(3-{2-[2-hydroxy-2-(4-hydroxy-3-hydroxymethyl-phenyl)-ethylamino]-propyl}-phenyl)-acetamide
optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzo ate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

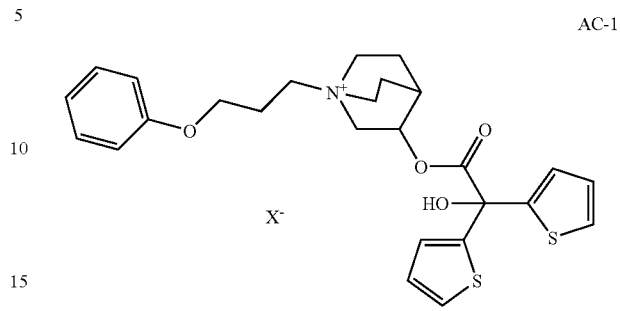

AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

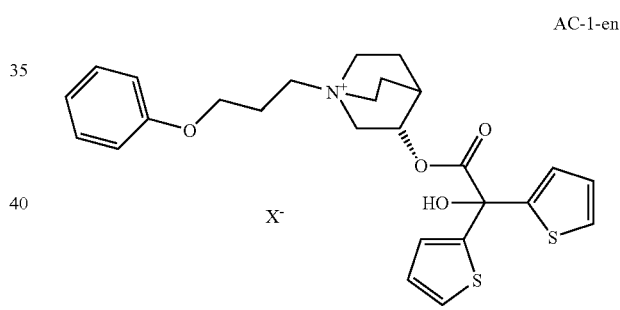

AC-1-en wherein $X^-$ may have the above-mentioned meanings. Other preferred anticholinergics are selected from the salts of formula AC-2

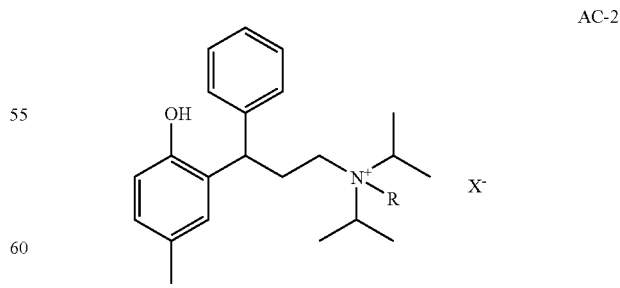

AC-2 wherein R denotes either methyl or ethyl and wherein $X^-$ may have the above-mentioned meanings. In an alternative embodiment the compound of formula AC-2 may also be present in the form of the free base AC-2-base.

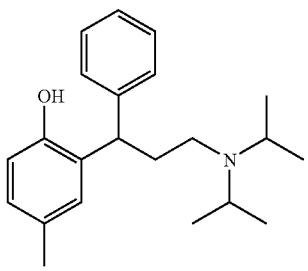

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3 S-yl)6,9-difluoro-11-hydroxy-16-methyl-3-oxo-17-propionyloxy-androsta-1,4-diene-17-carbothionate,
cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate
optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide
(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-S-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxy-phenyl)cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate
(S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3,4-c]-1,2,4-triazolo[4,3-a]pyridine
9-cyclopentyl-5,6-dihydro-7-ethyl-3-(tert-butyl)-9H-pyrazolo[3,4-c]-1,2,4-triazolo[4,3-a]pyridine
optionally in the form of the racemates, enantiomers or diastereomers thereof and optionally in the form of the pharmacologically acceptable acid addition salts thereof, the solvates and/or hydrates thereof. According to the invention the acid addition salts of the PDE4 inhibitors are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and
1-(((R)-(3-(2-(6,7-difluoro-2-quinolinyl)ethenyl)phenyl)-3-(2-(2-hydroxy-2-propyl)phenyl)thio)methylcyclopropane-acetic acid,
1-(((1 R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid
[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention these acid addition salts are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]-amino}-7-cyclopropylmethoxy-quinazoline 4-[(3-chloro-4-fluorophenyl)amino]-6-{[4-(N,N-diethylamino)-1-oxo-2-buten-1-yl]-amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluoro-phenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluorophenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yl-oxy}-7-methoxy-quinazoline 4-[(3-chloro-4-fluoro-phenyl)amino]-6-{1-[(methoxymethyl)carbonyl]-piperidin-4-yl-oxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline
4-[(3-chloro-4-fluoro-phenyl)amino]-6-{trans-4-[(dimethylamino)sulphonylamino]-cyclohexan-1-yloxy}-7-methoxy-quinazoline
4-[(3-chloro-4-fluoro-phenyl)amino]-6-{trans-4-[(morpholin-4-yl)carbonylamino]-cyclohexan-1-yloxy}-7-methoxy-quinazoline
4-[(3-chloro-4-fluoro-phenyl)amino]-6-{trans-4-[(morpholin-4-yl)sulphonylamino]-cyclohexan-1-yloxy}-7-methoxy-quinazoline
4-[(3-chloro-4-fluoro-phenyl)amino]-6-(tetrahydropyran-4-yloxy)-7-(2-acetylamino-ethoxy)-quinazoline
4-[(3-chloro-4-fluoro-phenyl)amino]-6-(tetrahydropyran-4-yloxy)-7-(2-methanesulphonylamino-ethoxy)-quinazoline
4-[(3-chloro-4-fluoro-phenyl)amino]-6-{1-[(piperidin-1-yl)carbonyl]-piperidin-4-yloxy}-7-methoxy-quinazoline
4-[(3-chloro-4-fluoro-phenyl)amino]-6-(1-aminocarbonylmethyl-piperidin-4-yloxy)-7-methoxy-quinazoline
4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline
4-[(3-chloro-4-fluoro-phenyl)amino]-6-(trans-4-ethanesulphonylamino-cyclohexan-1-yloxy)-7-methoxy-quinazoline
4-[(3-chloro-4-fluoro-phenyl)amino]-6-(1-methanesulphonyl-piperidin-4-yloxy)-7-ethoxy-quinazoline
4-[(3-chloro-4-fluoro-phenyl)amino]-6-(1-methanesulphonyl-piperidin-4-yloxy)-7-(2-methoxy-ethoxy)-quinazoline
4-[(3-chloro-4-fluoro-phenyl)amino]-6-[1-(2-methoxy-acetyl)-piperidin-4-yloxy]-7-(2-methoxy-ethoxy)-quinazoline
4-[(3-chloro-4-fluoro-phenyl)amino]-6-(cis-4-acetylamino-cyclohexan-1-yloxy)-7-methoxy-quinazoline
4-[(3-ethynyl-phenyl)amino]-6-[1-(tert.-butyloxycarbonyl)-piperidin-4-yloxy]-7-methoxy-quinazoline
4-[(3-ethynyl-phenyl)amino]-6-(tetrahydropyran-4-yloxy)-7-methoxy-quinazoline
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline
4-[(3-chloro-4-fluoro-phenyl)amino]-6-{cis-4-[(morpholin-4-yl)carbonylamino]-cyclohexan-1-yloxy}-7-methoxy-quinazoline
4-[(3-chloro-4-fluoro-phenyl)amino]-6-{1-[2-(2-oxopyrrolidin-1-yl)ethyl]-piperidin-4-yloxy}-7-methoxy-quinazoline
4-[(3-chloro-4-fluoro-phenyl)amino]-6-{1-[(morpholin-4-yl)carbonyl]-piperidin-4-yloxy}-7-(2-methoxy-ethoxy)-quinazoline
4-[(3-ethynyl-phenyl)amino]-6-(1-acetyl-piperidin-4-yloxy)-7-methoxy-quinazoline
4-[(3-ethynyl-phenyl)amino]-6-(1-methyl-piperidin-4-yloxy)-7-methoxy-quinazoline
4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxyethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline
4-[(3-chloro-4-fluoro-phenyl)amino]-6-(1-methanesulphonyl-piperidin-4-yloxy)-7-methoxy-quinazoline
4-[(3-chloro-4-fluoro-phenyl)amino]-6-(1-cyano-piperidin-4-yloxy)-7-methoxy-quinazoline
optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Any inhalable compounds, including also inhalable macromolecules as disclosed in EP 1 003 478, may be used as pharmaceutically effective substances, formulations or mixtures of substances. Preferably, substances, formulations or mixtures of substances administered by inhalation may be used for treating respiratory complaints.

In addition, the compound may come from the groups of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

The proportion of suspended drug in the finished preparation is between 0.001 and 5%, preferably 0.005 to 3%, particularly 0.01 to 2% (%=percent by weight).

In the case of ipratropium bromide monohydrate the suspensions according to the invention preferably contain between 0.001 to 1%, particularly 0.005 to 0.5% ipratropium. Particularly preferred according to the invention are suspensions which contain 0.01 to 0.1% ipratropium.

In the case of salbutamol and the salts thereof the suspensions according to the invention preferably contain between 0.005 to 5%, particularly 0.025 to 2.5% salbutamol. Particularly preferred according to the invention are suspensions which contain 0.05 to 1% salbutamol.

In the case of tiotropium bromide monohydrate the suspensions according to the invention preferably contain between 0.001 to 1%, particularly 0.0012 to 0.8% tiotropium. Preferred according to the invention are suspensions which contain 0.002 to 0.5%, particularly preferably 0.008 to 0.4% tiotropium.

By all the active substances, e.g. tiotropium or ipratropium, is meant in each case the free ammonium cation; by salbutamol is meant the salbutamol base.

The propellant gas suspensions according to the invention are characterised in that they contain tiotropium or ipratropium in the form of the crystalline monohydrates. Accordingly, the present invention preferably relates to suspensions which contain crystalline tiotropium bromide monohydrate or ipratropium bromide monohydrate.

The percentage amounts specified within the scope of the present invention are always percent by mass. If amounts by mass for tiotropium are expressed as percent by mass, the corresponding values for the crystalline tiotropium bromide monohydrate which is preferably used within the scope of the present invention may be obtained by multiplying by the conversion factor 1.2495. The same applies to ipratropium.

The propellant-containing inhalable aerosols or suspension formulations according to the invention may also contain other constituents such as surface-active agents (surfactants), adjuvants, antioxidants or flavourings.

The surface-active agents (surfactants) contained in the suspensions according to the invention are preferably selected from among polyethyleneglycols (PEG) and/or polyvinylpyrrolidones (PVP, povidone) and/or isopropyl myristate. Of the above-mentioned suspension adjuvants, PEG 200, PEG 400 and/or the polyvinylpyrrolidone K25 and/or isopropyl myristate are preferably used.

If the suspensions according to the invention contain surfactants these are preferably used in an amount of 0.005-5%, particularly preferably 0.01-1%.

If anhydrous propellant gases are used, a small amount of water is added to them according to the invention. However, it is also possible according to the invention to use water-containing propellant gases, which should have a specific water content when used. This water which is added to or present in the finished suspension formulation is different from water which is chemically bound in one of the active substances or excipients. This non-chemically bound water is also referred to as free water, to distinguish it from the water which is molecularly or chemically bound to the active substance.

It has been found that the suspended particles of active substance change when the water content is too low. On the other hand it has been found that the particle sizes also change if the water content is too high. The optimum water content may be determined individually for each substance. It has been found that the preferred amount of water in the propellant gas TG 227 ea or in mixtures of TG 227 ea with propellant gases selected from among propane, butane, pentane, dimethylether, $CHClF_2$, $CH_2F_2$, $CF_3CH_3$, isobutane, isopentane and neopentane, is generally 10 to 1000 ppm, particularly preferably 50 to 500 ppm, and most particularly preferably the amount of water is 100 to 450 ppm.

In the case of formulations containing ipratropium bromide monohydrate with propellant gas TG 227 ea the most preferred water content of the formulation is between 20 and 500 ppm, and the water content is particularly between 50 and 350 ppm.

In the case of tiotropium bromide monohydrate the preferred water content is comparable to that for ipratropium bromide monohydrate. The most preferred range is between 50 and 230 ppm.

It has also been found that the preferred quantity of water in the propellant gas TG 134 a or in mixtures of TG 134 a with propellant gases from the group propane, butane, pentane, dimethylether, $CHClF_2$, $CH_2F_2$, $CF_3CH_3$, isobutane, isopentane and neopentane is between 30 and 4000 ppm, particularly preferably between 150 and 2000 ppm and most particularly preferably between 350 and 1700 ppm.

In the case of formulations containing ipratropium monohydrate with propellant gas TG 134 a the most preferred water content of the formulation is between 70 and 1800 ppm, and in particular the water content is between 180 and 1300 ppm.

In the case of tiotropium monohydrate the preferred water content is similar to that for ipratropium bromide. The most preferred range is between 180 and 900 ppm.

If mixtures of the propellant gases TG 134 a and TG 227 ea are used, the preferred water contents are obtained from the mixing ratio of the two propellant gases.

According to the invention these amounts of water are added to the propellant gases or to the finished aerosol suspensions if the propellant gas, propellant gas mixture or the formulation does not contain any water (free water) in addition to the water chemically bound to the active substance. In the process, the water may have already been added to the propellant gas before the pharmaceutical suspension is prepared, or the pharmaceutical suspension may be prepared first with anhydrous propellant gas or propellant gas mixture and then the corresponding amount of water is added.

The amounts given in ppm are based on the liquefied propellant as the reference magnitude.

Within the scope of the present invention the term suspension formulation may be used instead of the term suspension. The two terms are to be regarded as equivalent within the scope of the present invention.

With a view to administration by inhalation it is essential to provide the active substances in finely divided form. For this purpose, the active substance is obtained in finely divided form either by grinding (micronising) or using other methods known in the prior art (e.g. Precipitation, spray-drying). Methods of micronising active substances are known in the art. Preferably after micronising the active substance has a mean particle size of 0.1 to 10 μm, preferably 0.5 to 6 μm, particularly preferably 1 to 5 μm.

The suspensions according to the invention may be prepared using methods known in the art. For this, the constituents of the formulation are mixed with the propellant gas or gases (optionally at low temperatures) and filled into suitable containers.

The above-mentioned propellant-containing suspensions according to the invention may be administered using inhalers known in the art (pMDIs=pressurized metered dose inhalers). Accordingly, in another aspect, the present invention relates to pharmaceutical compositions in the form of suspensions as hereinbefore described combined with one or more inhalers suitable for administering these suspensions. Moreover the present invention relates to inhalers, characterised in that they contain the propellant-containing suspensions according to the invention described hereinbefore.

The present invention also relates to containers (e.g. cartridges) which are fitted with a suitable valve adjusted before use with regard to the water content.

The containers may be used in a suitable inhaler and contain one of the above-mentioned propellant-containing suspensions according to the invention. Suitable containers (e.g. cartridges) and processes for filling these cartridges with the propellant-containing suspensions according to the invention are known in the art.

In view of the pharmaceutical activity of anticholinergics the present invention also relates to the use of the suspensions according to the invention for preparing a pharmaceutical composition for inhalation or nasal administration, preferably for preparing a pharmaceutical composition for inhalative or nasal treatment of diseases in which anticholinergics may develop a therapeutic benefit.

Particularly preferably the present invention also relates to the use of the suspensions according to the invention for preparing a pharmaceutical composition for the inhalative treatment of respiratory complaints, preferably asthma, COPD, mucoviscidosis, cystic fibrosis; and also systemic complaints, such as pain, migraine, high blood pressure, erectile disorders.

The Examples that follow serve to illustrate the present invention in more detail, by way of example, without restricting it to their contents.

EXAMPLES OF FORMULATIONS

The formulations in the Examples each contain between 100 and 350 ppm water in addition to the ingredients specifically listed.

Example 1

| ingredient | percent by weight | g/container |
|---|---|---|
| salbutamol sulphate | 0.171 | 0.0312 |
| ipratropium bromide monohydrate | 0.030 | 0.0055 |
| polyvinylpyrrolidone K25 | 0.100 | 0.0183 |
| TG 227 ea | 99.700 | 18.244 |
| total | 100.000 | 18.2987 |

Example 2

| ingredient | percent by weight | g/container |
|---|---|---|
| salbutamol sulphate | 0.171 | 0.0312 |
| ipratropium bromide monohydrate | 0.030 | 0.0055 |
| polyvinylpyrrolidone K25 | 0.100 | 0.0183 |
| isopropyl myristate | 0.300 | 0.0548 |
| TG 227 ea | 99.399 | 18.1531 |
| total | 100.000 | 18.2628 |

Example 3

| ingredient | percent by weight | g/container |
|---|---|---|
| salbutamol sulphate | 0.171 | 0.0312 |
| ipratropium bromide monohydrate | 0.030 | 0.0055 |
| polyvinylpyrrolidone K25 | 0.100 | 0.0183 |
| polyethyleneglycol 200 | 0.300 | 0.0549 |
| TG 227 ea | 99.399 | 18.1751 |
| total | 100.000 | 18.2849 |

Example 4

| ingredient | percent by weight | g/container |
| --- | --- | --- |
| salbutamol sulphate | 0.178 | 0.0312 |
| ipratropium bromide monohydrate | 0.031 | 0.0055 |
| polyvinylpyrrolidone K25 | 0.100 | 0.0176 |
| polyethyleneglycol 400 | 0.300 | 0.0527 |
| TG 134a | 28.000 | 4.9145 |
| TG 227 ea | 70.391 | 12.5304 |
| total | 100.000 | 17.5517 |

Example 5

| ingredient | percent by weight | g/container |
| --- | --- | --- |
| salbutamol sulphate | 0.213 | 0.0312 |
| ipratropium bromide monohydrate | 0.037 | 0.0055 |
| polyvinylpyrrolidone K25 | 0.100 | 0.0146 |
| TG 227 ea | 99.650 | 14.5873 |
| total | 100.000 | 14.6386 |

Example 6

| ingredient | percent by weight | g/container |
| --- | --- | --- |
| salbutamol sulphate | 0.214 | 0.0312 |
| ipratropium bromide monohydrate | 0.037 | 0.0055 |
| polyvinylpyrrolidone K25 | 0.100 | 0.0146 |
| isopropyl myristate | 0.300 | 0.0438 |
| TG 227 ea | 99.349 | 14.5147 |
| total | 100.000 | 14.6098 |

Example 7

| ingredient | percent by weight | g/container |
| --- | --- | --- |
| salbutamol sulphate | 0.213 | 0.0312 |
| ipratropium bromide monohydrate | 0.037 | 0.0055 |
| polyvinylpyrrolidone K25 | 0.100 | 0.0146 |
| polyethyleneglycol 200 | 0.300 | 0.0439 |
| TG 227 ea | 99.350 | 14.5323 |
| total | 100.000 | 14.6275 |

Example 8

| ingredient | percent by weight | g/container |
| --- | --- | --- |
| salbutamol sulphate | 0.222 | 0.0312 |
| ipratropium bromide monohydrate | 0.039 | 0.0055 |
| polyvinylpyrrolidone K25 | 0.100 | 0.0140 |
| polyethyleneglycol 400 | 0.300 | 0.0421 |
| TG 134a | 28.000 | 3.9315 |
| TG 227 ea | 71.339 | 10.0167 |
| total | 100.000 | 14.0410 |

The invention claimed is:

1. A propellant-containing aerosol suspension comprising: particles of active substance with chemically bound water, at least 85 wt. % of a propellant gas or a propellant gas mixture with TG 227 ea and/or TG 134 a or in admixture with at least one other propellant gas selected from the group consisting of propane, butane, pentane, dimethylether, $CHClF_2$, $CH_2F_2$, $CF_3CH_3$, isobutane, isopentane and neopentane, wherein the aerosol suspension contains the surface-active substance polyvinylpyrrolidone in an amount of 0.005-5% by mass of the suspension and does not contain polyethylene glycol and does not contain ethanol;

wherein when the propellant gas mixture comprises TG 227 ea, the suspension contains between 10 and 1000 ppm water;

wherein when the propellant gas mixture comprises TG 134 a, the suspension contains between 30 and 4000 ppm water;

and wherein when the propellant gas mixture comprises both TG 227 ea and TG 134 a, the suspension contains a water content obtained from the mixing ratio of the two propellant gases.

2. The aerosol suspension according to claim 1, wherein it contains polyvinylpyrrolidone K25 and/or isopropyl myristate.

3. The aerosol suspension according to claim 2, wherein the active substance is selected from the group consisting of betamimetics, anticholinergics, steroids, antiallergics, derivatives of ergot alkaloids, triptanes, CGRP-antagonists, phosphodiesterase-V inhibitors, phosphodiesterase-IV inhibitors, LTD4-antagonists, EGFR-kinase inhibitors, and combinations of said active substances.

4. The aerosol suspension according to claim 1, wherein the suspension contains an anticholinergic as active substance.

5. The aerosol suspension according to claim 4, wherein the suspension additionally contains a betamimetic as active substance.

6. The aerosol suspension according to claim 1, wherein it contains as further ingredients surface-active substances (surfactants), adjuvants, antioxidants and/or flavourings.

7. The aerosol suspension according to claim 6, wherein it contains as adjuvants one or more compounds selected from the group consisting of alanine, albumin, ascorbic acid, aspartame, betaine, cysteine, phosphoric acid, nitric acid, hydrochloric acid, sulphuric acid and citric acid.

8. The aerosol suspension according to claim 7, wherein it contains as antioxidants one or more compounds selected from the group consisting of ascorbic acid, citric acid, sodium edetate, editic acid, tocopherols, butylhydroxytoluene, butylhydroxyanisol and ascorbylpalmitate.

9. A process for preparing aerosol suspensions according to claim 1, comprising preparing an aerosol suspension with anhydrous propellant gas or propellant gas mixture and then adding water.

10. The aerosol suspension according to claim 4, wherein the suspension contains ipratropium salt or tiotropium salt.

11. The aerosol suspension according to claim 10, wherein the suspension contains ipratropium bromide or tiotropium bromide.

12. The aerosol suspension according to claim 11, wherein the suspension contains ipratropium bromide monohydrate or tiotropium bromide monohydrate.

13. The aerosol suspension according to claim 5, wherein the suspension additionally contains salbutamol or fenoterol in each case as a base or salt.

14. The aerosol suspension according to claim 13, wherein the suspension additionally contains salbutamol sulphate or fenoterol hydrobromide.

15. The aerosol suspension according to claim 5, wherein the amount of active substance is between 0.005 to 3%.

16. The aerosol suspension according to claim 15, wherein the amount of active substance is between 0.01 to 2% by mass of the suspension.

17. The aerosol suspension according claim 1, wherein for the propellant gas TG 227 ea or mixtures with this propellant gas the amount of water is between 50 and 500 ppm.

18. The aerosol suspension according claim 17, wherein for the propellant gas TG 227 ea or mixtures with this propellant gas the amount of water is between 100 and 450 ppm.

19. The aerosol suspension according to claim 1, wherein for the propellant gas TG 134 a or mixtures with this propellant gas the amount of water is between 150 and 2000 ppm.

20. The aerosol suspension according to claim 19, wherein for the propellant gas TG 134 a or mixtures with this propellant gas the amount of water is between 350 and 1700 ppm.

21. A method of treating a disease selected from the group consisting of asthma, COPD, mucoviscidosis, cystic fibrosis, pain, migraine, hypertension and erectile disorder comprising administering a therapeutically effect amount of an aerosol suspension according to claim 1.

22. The aerosol suspension according to claim 1, wherein the active substance comprises an anticholinergic and a betamimetic.

23. The aerosol suspension according to claim 1, wherein the active substance is tiotropium bromide.

* * * * *